United States Patent
Barthelet et al.

(10) Patent No.: US 10,961,172 B2
(45) Date of Patent: Mar. 30, 2021

(54) METHOD FOR SIMULTANEOUSLY ELIMINATING ISOBUTANAL AND A FEEDSTOCKS BY ADSORPTION ON A ZEOLITE MATERIAL

(71) Applicants: IFP Energies nouvelles, Rueil-Malmaison (FR); TOTAL RESEARCH & TECHNOLOGY FELUY, Seneffe (BE)

(72) Inventors: Karin Barthelet, Lyons (FR); Emmanuelle Bracco, Condrieu (FR); Vincent Coupard, Villeurbanne (FR); Nikolai Nesterenko, Nivelles (BE)

(73) Assignees: IFP Energies nouvelles, Rueil-Malmaison (FR); TOTAL RESEARCH & TECHNOLOGY FELUY, Seneffe (BE)

( * ) Notice: Subject to any disclaimer, the term of this patent is extended or adjusted under 35 U.S.C. 154(b) by 0 days.

(21) Appl. No.: 16/772,626

(22) PCT Filed: Nov. 30, 2018

(86) PCT No.: PCT/EP2018/083124
§ 371 (c)(1),
(2) Date: Jun. 12, 2020

(87) PCT Pub. No.: WO2019/115251
PCT Pub. Date: Jun. 20, 2019

(65) Prior Publication Data
US 2020/0385324 A1    Dec. 10, 2020

(30) Foreign Application Priority Data
Dec. 13, 2017 (FR) .................................. 1762090

(51) Int. Cl.
*C07C 1/24* (2006.01)
*C07C 7/13* (2006.01)

(52) U.S. Cl.
CPC ...................... *C07C 7/13* (2013.01)

(58) Field of Classification Search
CPC ......... C07C 11/08; C07C 1/24; C07C 5/2506; C07C 5/2708; C07C 6/04; C07C 7/14866;
(Continued)

(56) References Cited

U.S. PATENT DOCUMENTS

| 8,450,543 B2 * | 5/2013 | Peters ..................... C07C 15/04 585/240 |
| 9,272,965 B2 * | 3/2016 | Cross, Jr. ................ C07C 11/02 |

(Continued)

FOREIGN PATENT DOCUMENTS

EP      2547639 B1    8/2016

OTHER PUBLICATIONS

International Search Report PCT/EP2018/083124 dated Mar. 1, 2019 (pp. 1-2) and International Search report (pp. 1-83).

*Primary Examiner* — Sharon Pregler
(74) *Attorney, Agent, or Firm* — Millen White Zelano and Branigan, PC; Csaba Henter

(57) ABSTRACT

A process for purifying an olefinic feedstock containing olefins with 4 carbon atoms and impurities including isobutanal, ethanol and acetone, the process including a pre-treatment containing at least one step of eliminating the ethanol and the water present in the olefinic feedstock and a step of simultaneously eliminating the isobutanal and the acetone, by passing the feedstock from the pre-treatment over at least one fixed bed of at least one adsorbent containing at least one material with a zeolite framework, the material with a zeolite framework being chosen from zeolites, AlPOs, SAPOs and mixtures thereof; the step of
(Continued)

simultaneously eliminating the isobutanal and the acetone being carried out at a temperature of between 0 and 200° C., at a pressure of 0.1 to 10 MPa and with an hourly space velocity of the feedstock over the fixed bed of 0.1 to 10 $h^{-1}$.

13 Claims, 1 Drawing Sheet

(58) Field of Classification Search
CPC ..... C07C 7/14891; C07C 7/177; C07C 11/06; C07C 11/09; C07C 2521/04; C07C 2521/08; B01J 21/04; B01J 2229/36; B01J 2229/37; B01J 29/40; B01J 29/65; B01J 37/28; Y02P 20/127; Y02P 20/52; Y02P 20/10
See application file for complete search history.

(56) References Cited

U.S. PATENT DOCUMENTS

| | | | |
|---|---|---|---|
| 2013/0245348 A1* | 9/2013 | Vermeiren | C07C 6/04 585/324 |
| 2019/0177624 A1* | 6/2019 | Barthelet | C07C 7/005 |

* cited by examiner

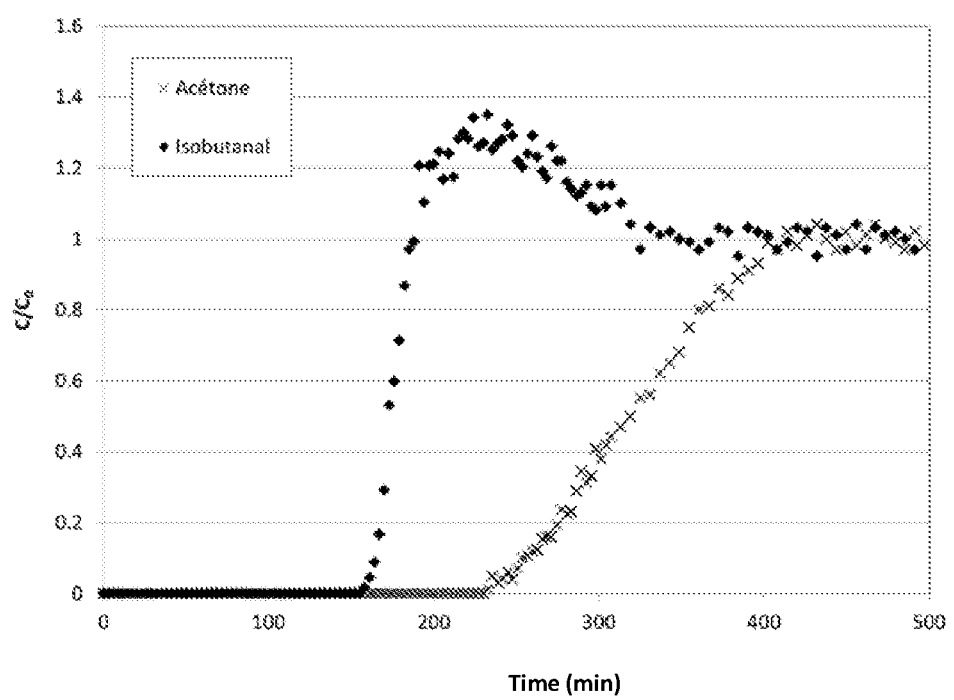

METHOD FOR SIMULTANEOUSLY ELIMINATING ISOBUTANAL AND A FEEDSTOCKS BY ADSORPTION ON A ZEOLITE MATERIAL

FIELD OF THE INVENTION

The present invention relates to a process for purifying an olefinic feedstock, comprising a step of simultaneously eliminating aldehydes and ketones from an olefinic feedstock, carried out at low temperature (less than or equal to 200° C.) by adsorption on an adsorbent comprising a material with a zeolite framework. More particularly, the invention relates to a process for purifying an olefinic feedstock comprising olefins with 4 carbon atoms and impurities comprising isobutanal, ethanol and acetone, said process comprising a step of simultaneously eliminating isobutanal and acetone by passing said olefinic feedstock, treated beforehand, over a fixed bed comprising at least one material with a zeolite framework. The pre-treatment of the olefinic feedstock comprises at least the elimination of the ethanol and of the water, contained in the olefinic feedstock.

The invention advantageously applies to the treatment of effluents from the conversion of oxygen-containing compounds and in particular to the treatment of the effluent resulting from the dehydration of a butanol isomer, in particular isobutanol, or of a mixture of butanol isomers comprising isobutanol.

PRIOR ART

The butenes produced by dehydration of alcohol, in particular by dehydration of a butanol isomer, in particular isobutanol, or of a mixture of butanol isomers comprising isobutanol, generally contain a few hundred ppm by mass of isobutanal, ethanol and acetone. However, to comply with the specifications imposed on butenes, it is necessary to eliminate them. Indeed, the butenes produced may be intended to be sent to a metathesis unit which uses a catalyst that does not tolerate more than 10 ppm by weight of oxygen. The term "ppm by weight of oxygen" or "oxygen content" is understood to mean the mass content of oxygen atom contained in the mixture in question. This oxygen content can be calculated from the mass or molar composition of oxygen-containing hydrocarbon-based compounds of the mixture in question.

Patent EP 2 547 639 B1, which describes a process for metathesis of alkenes, thus explains that many pollutants present in the metathesis feedstock are responsible for the drop in activity of the catalyst.

To reach very low levels of impurity concentration, one of the techniques often used is adsorption on a solid implemented on a fixed bed. This nevertheless involves finding the right adsorbent(s) to allow the elimination of all the impurities present.

Patent EP 2 547 639 B1 mentions aluminas and zeolites as potential adsorbents. However, no link is given between the nature of the compounds to be eliminated and the choice of adsorbent for obtaining an effective treatment of alkenes.

The article C. C. Brunchi et. al., Ind. Eng. Chem. Res., 2012, 51, 16697-16708, describes the batchwise co-adsorption of a mixture of volatile organic compounds (VOCs), butanal, 2-ethyl-2-hexanal, 2,6-dimethylcyclohexanone, 2,4,6-trimethylphenol and 2,4,6-trimethylanisole, in toluene. The results obtained show that the NaY zeolite makes it possible to adsorb butanal and 2,6-dimethylcyclohexanone. However, the good capacity for adsorption by NaY of butanal present in an aromatic feedstock such as toluene does not make it possible to deduce that NaY could eliminate isobutanal from an olefinic feedstock. Indeed, it is not easy to predict the capacity and the selectivity of adsorption of different molecules present in different solvents.

The document Rouquerol J. et al.; "Adsorption by Powders & Porous Solids: Principle, methodology and applications (second edition)", Chapter 12. "Adsorption by clays, pillared clays, zeolites and aluminophosphates", 467-527, Academic Press, 2014, in fact teaches that the mechanism of sorption of molecules by zeolites in general and by NaY in particular is that of physical adsorption, or physisorption. The physisorption phenomenon can be defined as the attaching of adsorbate molecules on the surface of an adsorbent by the implementation of weak interactions of the type Van der Waals and/or electrostatic interactions of polarization, dipole and quadrupole for adsorbents having an ionic structure. These interactions are not specific. In fact, it is not easy to predict the capacity and even less the selectivity of adsorption of different molecules present in different solvents.

The weak adsorption by NaY of 2-ethyl-2-hexanal compared to butanal (twice as weak), shown by C. C. Brunchi et. al., illustrates very well this non-obviousness of the selectivity of adsorption by a zeolite of different molecules of the same chemical family.

The applicant has demonstrated that the use in a fixed bed of at least one adsorbent comprising at least one material with a zeolite framework makes it possible to simultaneously eliminate isobutanal and acetone from olefinic feedstocks comprising olefins with 4 atoms of carbon, from which ethanol and water have been eliminated beforehand.

The present invention thus relates to a process for purifying an olefinic feedstock comprising olefins with 4 carbon atoms, in particular resulting from the dehydration of a butanol isomer, in particular isobutanol, or of a mixture of butanol isomers comprising isobutanol, allowing the elimination of isobutanal, acetone and ethanol impurities, contained in an amount of a few hundred ppm by mass in said feedstock.

SUMMARY OF THE INVENTION

In particular, the present invention relates to a process for purifying an olefinic feedstock comprising olefins with 4 carbon atoms and impurities including isobutanal, ethanol and acetone, said process comprising:

a) a pre-treatment step comprising a step of eliminating the ethanol and the water; and b) a step of simultaneously eliminating isobutanal and acetone, by passing the pretreated feedstock from step a) over at least one fixed bed of at least one adsorbent comprising at least one material with a zeolite framework, said material with a zeolite framework being chosen from the group consisting of: zeolites, AlPOs, SAPOs and mixtures thereof;

said material with a zeolite framework having at least cages or channels of which at least one opening is defined by a ring comprising at least 10 oxygen atoms (10MR);

said step b) being carried out at a temperature of between 0 and 200° C., at a pressure of 0.1 to 10 MPa and with an hourly space velocity (HSV) of the pretreated feedstock from step a) over the fixed bed of between 0.1 and 10 $h^{-1}$.

The invention advantageously applies to the treatment of effluents from the conversion of oxygen-containing compounds and in particular to the treatment of the effluent resulting from the dehydration of a butanol isomer, in particular isobutanol, or of a mixture of butanol isomers comprising isobutanol. In particular, the invention applies to the treatment of the effluent resulting from the dehydration of isobutanol alone or as a mixture with other butanol isomers. Advantageously, the use of a fixed bed of at least one specific adsorbent, said adsorbent comprising at least one material with a zeolite framework, under the particular conditions according to the invention, makes it possible to eliminate the impurities, in particular isobutanal and acetone, contained in the mixture of butenes resulting from the dehydration of isobutanol or of a mixture of butanol isomers comprising isobutanol.

The purification process according to the invention thus makes it possible to obtain, by virtue of the use of a fixed bed of specific adsorbent and under optimized conditions, an oxygen content, indicative of the mass content of oxygen-containing hydrocarbon-based impurities, in the mixture of olefins at the end of the purification, of less than 50 ppm by mass, preferably less than or equal to 30 ppm by mass, preferably less than or equal to 15 ppm by mass, preferably less than or equal to 10 ppm by mass and very preferably less than or equal to 1 ppm by mass. The term "ppm by weight of oxygen" or "oxygen content" is understood to mean the mass content of oxygen atom contained in the mixture in question. This oxygen content can be calculated from the oxygen-containing hydrocarbon-based compound mass or molar composition of the mixture in question. Advantageously, the process according to the invention makes it possible to obtain mass contents of oxygen-containing hydrocarbon-based impurities, such as isobutanal, ethanol and acetone, in the mixture of olefins at the end of the purification, of less than 50 ppm, preferably less than or equal to 30 ppm, preferably less than or equal to 15 ppm, preferably less than or equal to 10 ppm and very preferably less than or equal to 1 ppm.

Unlike aluminum adsorbents, the adsorbent comprising at least one material with a zeolite framework can carry out the treatment of olefinic feedstocks containing isobutanal and acetone without the latter reacting in an undesired manner with the isobutanal present.

In the process according to the invention, the adsorbent comprising a material with a zeolite framework can undergo several regeneration cycles and can retain significant capture capacities, which can have a real economic advantage.

DESCRIPTION OF THE INVENTION

In the present invention, the term "content of oxygen-containing hydrocarbon-based impurities" or "mass content of oxygen-containing hydrocarbon-based impurities" of a feedstock or an effluent (initial feedstock, olefinic feedstock or effluent at the end of the process) is intended to mean the mass of oxygen-containing hydrocarbon-based impurities, such as isobutanal, ethanol and acetone, per unit mass of the feedstock or the effluent in question. As the usual method for determining the content of each of the oxygen-containing hydrocarbon-based impurities, mention will for example be made of the UOP 960 method which uses gas phase chromatography.

It should be noted that the oxygen of the water, present in dissolved form in the feedstock or the effluent, is not counted in the content of oxygen-containing hydrocarbon-based impurities. The water content present in dissolved form in the feedstock or the effluent can be determined by a specific technique, for example according to the Karl Fischer method (cf. Analysis of residual solvents in pharmaceutical products, engineering techniques P3260v1 M. Bauer Oct. 9, 2001).

In the present invention, the term "hourly space velocity (HSV) of the feedstock over the fixed bed" is intended to mean the ratio between the hourly space flow rate of the feedstock to be treated and the volume of the reactor.

According to the present invention, the expression "between . . . and . . . " means that the limiting values of the interval are included in the range of values which is described. Should this not be the case and should be limiting values not be included in the range described, such a clarification will be given by the present invention.

The present invention consists of a process for purifying an olefinic feedstock comprising olefins with 4 carbon atoms and impurities including isobutanal, ethanol and acetone, said process comprising:

a) a pre-treatment step comprising a step of eliminating the ethanol and the water; and b) a step of simultaneously eliminating the isobutanal and the acetone by passing the pretreated feedstock from step a) over at least one fixed bed of at least one adsorbent comprising at least one material with a zeolite framework, said material with a zeolite framework being chosen from the group consisting of: zeolites, AlPOs, SAPOs and mixtures thereof;

said material with a zeolite framework having at least cages or channels of which at least one opening is defined by a ring comprising at least 10 oxygen atoms (10MR);

said step b) being carried out at a temperature of between 0 and 200° C., at a pressure of 0.1 to 10 MPa and with an hourly space velocity (HSV) of the pretreated feedstock from step a) over the fixed bed of between 0.1 and 10 $h^{-1}$.

The Olefinic Feedstock

The olefinic feedstock treated by the purification process according to the invention is a mixture of olefins. This mixture may contain linear olefins, branched olefins or a mixture of linear and branched olefins.

The olefinic feedstock is characterized by its very high olefin content. It preferably contains at least 95% by weight, preferably at least 97% by weight, of its dry weight in olefins. The high content of olefins gives this cut a particularly high reactivity, as much in the downstream exploitation steps as in the conversion or purification steps to which it is subjected.

The olefins present in the feedstock are compounds mainly with 4 carbon atoms, more particularly butenes, in particular a mixture of n-butenes and of isobutene.

The feedstock treated according to the invention may also contain non-olefinic compounds among which may be, in addition to water, organic hydrocarbon-based compounds (impurities). The organic hydrocarbon-based compounds may be paraffins, dienes and oxygen-containing organic compounds, among which mention may be made of aldehydes, ketones, alcohols, acetals, ether esters, furans, carboxylic acids.

More particularly, the feedstock treated according to the invention comprises olefins with 4 carbon atoms and oxygen-containing hydrocarbon-based impurities comprising isobutanal, ethanol and acetone.

According to a variant of the invention, the olefinic feedstock results from the conversion of oxygen-containing compounds. Preferably, the olefinic feedstock treated according to the invention results from the dehydration of isobutanol or of a mixture of butanol isomers comprising isobutanol. Preferably, the olefinic feedstock treated according to the invention results from the dehydration of a butanol isomer, in particular isobutanol, or of a mixture of butanol isomers comprising isobutanol. Typically, the butenes produced by dehydration of isobutanol or of a mixture of butanol isomers comprising isobutanol contain a few hundred ppm of isobutanal, ethanol and acetone.

Step a)

According to the invention, the olefinic feedstock undergoes a pre-treatment comprising at least one step of eliminating the ethanol and water that the olefinic feedstock could contain. This pre-treatment makes it possible to increase the selectivity of the adsorbent, used in the subsequent step b) and comprising at least one material with a zeolite framework, with respect to isobutanal and acetone. The pre-treatment therefore makes it possible to optimize the capacity for capture of isobutanal and acetone by the adsorbent in step b).

Indeed, the applicant has discovered that, among the impurities present in the feedstock, some are incompatible with the use of an adsorbent based on a material comprising a zeolite framework, such as the NaY zeolite for example. In particular, the presence of ethanol and/or water in the feedstock in particular reduces the performance levels of the adsorbent comprising a material with a zeolite framework. It is thus necessary to eliminate these impurities from the olefinic feedstock, before passing it over the adsorbent comprising at least one material with a zeolite framework.

The ethanol and water contained in the olefinic feedstock are eliminated by any method known to those skilled in the art. In particular, the ethanol can be eliminated by distillation or by washing with water and the water can be eliminated by adsorption on a molecular sieve, for example of type 3A. For example, the ethanol is eliminated by washing the olefinic feedstock with water, followed by drying, for example on a sieve of type 3A, as is conventionally carried out in the etherification processes described, for example, in the book "Les biocarburants, état des lieux, perspectives et enjeux du développement" ["Biofuels, inventory, perspectives and challenges of development"], D. Ballerini, FIG. 2.13, page 109.

The elimination of water can be carried out simultaneously with the elimination of ethanol. It can also be carried out prior to or following the elimination of ethanol.

Advantageously, at the end of the pre-treatment (step a), the olefinic feedstock contains less than 10 ppm by mass, preferably less than 1 ppm by mass, of water, and less than 10 ppm by mass, preferably less than 1 ppm by mass, of ethanol. Furthermore, more particularly, the olefinic feedstock is devoid of ethanol and water.

The Adsorbent with a Zeolite Framework

In accordance with the invention, the purification process comprises passing the olefinic feedstock through a reactor comprising at least one fixed bed of at least one specific adsorbent.

According to the invention, the adsorbent comprises at least one material with a zeolite framework. The use of the adsorbent with a zeolite framework makes it possible to avoid the unwanted condensation reaction of isobutanal with acetone, unlike other types of adsorbents such as, for example, aluminum adsorbents.

The material with a zeolite framework according to the invention comprises at least one tetravalent element X chosen from silicon, tin, titanium and germanium. The tetravalent element X present in the material with a zeolite framework according to the invention is preferably chosen from silicon and germanium and, even more preferably, said element X is silicon.

In place of the tetravalent element X, the material with a zeolite framework according to the invention can, according to a particular embodiment of the invention, comprise a pentavalent element, such as phosphorus.

The material with a zeolite framework according to the invention also comprises, and according to a preferred embodiment of said material with a zeolite framework, at least one trivalent element T chosen from aluminum, iron, boron, gallium and indium. Preferably, the element T is aluminum.

According to the invention, the material with a zeolite framework is advantageously chosen from the group consisting of: zeolites, AlPOs, SAPOs and mixtures thereof.

Advantageously, the material with a zeolite framework has at least cages or channels of which the opening is defined by a ring with at least 10 oxygen atoms (10MR), preferably at least 12 oxygen atoms (12MR). In particular, the material with a zeolite framework has only cages or channels of which the opening is defined by a ring with at least 10 oxygen atoms (10MR), preferably at least 12 oxygen atoms (12MR).

In an embodiment according to the invention, the material with a zeolite framework is chosen from the group consisting of: AlPO-4, AlPO-5, AlPO-8, AlPO-11, JDF-20, VPI-5, SAPO-11, SAPO-40 or SAPO-37.

In another embodiment according to the invention, the material with a zeolite framework is a zeolite. Preferably, the material with a zeolite framework has a structural type chosen from the types FAU, BEA, MOR, MFI, FER, EMT, TON, SZR, LTL (in accordance with the codes assigned by the Structures Commission of the International Zeolite Association (IZA) (see http://www.iza-structure.org/databases/). Preferably, the material with a zeolite framework is of structural type FAU, MFI, BEA, LTL or MOR, for example type Y, X, ZSM-5, beta, L, mordenite or mixtures thereof. Even more preferably, the material with a zeolite framework is of type FAU, in particular Y or X.

Advantageously, the material with a zeolite framework has one or more types of charge-compensating cations in its cages or channels, these compensating cations being able to help the selectivity of the adsorbent. Preferably, the charge-compensating cation(s) are chosen from alkali and alkaline-earth metals. Very preferably, the charge-compensating cation(s) are alkali metals, in particular sodium ions. The charge of the material with a zeolite framework is not compensated for by protons.

The material with a zeolite framework advantageously has a micropore volume, determined by application of the standard ASTM D4365, of between 0.01 and 0.5 cm$^3 \cdot$g$^{-1}$, preferably between 0.05 and 0.45 cm$^3 \cdot$g$^{-1}$.

The specific surface area of the material with a zeolite framework according to the invention, determined by the BET method by application of the standard ASTM 4365, is advantageously between 200 and 1000 m$^2 \cdot$g$^{-1}$, preferably between 250 and 800 m$^2 \cdot$g$^{-1}$, more preferably between 300 and 700 m$^2 \cdot$g$^{-1}$.

Preferably, the material with a zeolite framework is formed, in the form of grains which can be of different shapes and sizes, according to any method known to those skilled in the art.

According to a variant of the invention, the zeolite material is formed with a binder. The binder content is then between 5 and 30% by weight, preferably between 10 and 25% by weight of the weight of the adsorbent formed. The binder is preferably chosen from all binders known to those skilled in the art; it can be chosen from the families of simple or mixed refractory oxides or hydroxides, clays, active carbons, and crosslinked vinyl resins. Preferably, the binder is a clay and, more particularly, the binder is a zeolitizable clay, that is to say that, by means of an appropriate treatment, the clay is converted into a zeolite, identical to or different than that formed, thus increasing the adsorption capacity of the adsorbent. The zeolitization can be carried out, for example, by treatment of the formed adsorbent with sodium hydroxide followed by calcination.

Advantageously, the adsorbent is used in the purification process according to the invention in the form of a stack of separate individual particles or in the form of one or more multichannel monoliths installed in series or in parallel.

In the case where the adsorbent is used in the form of a stack of separate individual particles, it is in the form of beads or multilobed cylinders, preferably with a number of lobes of between 2 and 5 or in the form of rings, hollow cylinders, hollow rings, Raschig rings, serrated hollow cylinders, crenellated hollow cylinders, cartwheels, Berl saddles or multi-hole cylinders, alone or as a mixture.

In the case where the adsorbent is used in the form of one or more multichannel monoliths installed in series or in parallel, it is preferably in the form of a multichannel monolith of honeycomb type, the channels being able to be of square, hexagonal, circular or oval cross-section. The surface of the monolith channels can be smooth, grooved or rough to promote intimate contact of the fluid to be treated with the surface of the monolith channels. The channel density can preferably vary from 5 cpsi to 400 cpsi (cpsi=channel per square inch) (respectively from approximately 0.8 to approximately 62.0 channels per cm$^2$). Alternatively, the monolith can consist of ceramic foam. The pore density of the ceramic foam is between 10 ppi and 60 ppi, and preferably between 10 and 30 ppi (ppi=pores per inch) (respectively between approximately 3.9 and approximately 23.6 pores per cm and preferably between approximately 3.9 and approximately 11.8 pores per cm).

The cross-section of the monolith must be equal to the internal cross-section of the reactor containing the bed of adsorbents in order to force the entire flow to be treated to circulate inside the channels of the monolith.

Advantageously, the fixed bed can comprise adsorbents exhibiting one or more types of forming. The adsorbent comprising the material with a zeolite framework can be used alone or as a mixture with one or more other adsorbent(s).

It is particularly advantageous to superimpose different adsorbents, in particular of different nature and/or different forming, in at least two different fixed beds of variable height, the adsorbents having the lowest void fraction, the void fraction being defined as the ratio of the difference between the volume of the reactor and the volume of solid over the volume of reactor (that is to say having the smallest volume filled by the adsorbent in question, relative to the volume of the reactor) preferably being used in the first fixed bed(s), at the inlet of the reactor in order to carry out a sort of filtration of the feedstock during its passage through the bed(s). Different adsorbents can also be mixed within one and the same bed.

According to one embodiment of the invention, the adsorbent can be activated, in particular in situ, just before its first use in the process according to the invention, according to any one of the methods known to those skilled in the art. Advantageously, the activation is carried out by passing a gas heated between 100 and 500° C. The gas used can be a combustion gas, air or nitrogen. Preferably, the activation gas is nitrogen.

Step b)

According to the invention, the process for purifying the olefinic feedstock, in particular the step of simultaneously eliminating the isobutanal and the acetone, is carried out at a temperature of between 0° C. and 200° C., preferably between 10 and 100° C. and preferably between 20 and 60° C., for example at 30° C., at a pressure of between 0.1 and 10 MPa, preferably between 0.3 and 5 MPa and with an hourly space velocity (HSV) of said feedstock over said fixed bed of between 0.1 and 10 h$^{-1}$ and preferably between 0.2 and 5 h$^{-1}$.

Under these conditions and by virtue of the specific adsorbent used in the purification process according to the invention, the adsorption of aldehydes and ketones, in particular isobutanal and acetone, is observed at the surface of the adsorbent at satisfactory capacities.

The purification process according to the invention, by virtue in particular of the specific adsorbent used under the particular conditions as defined, advantageously makes it possible to capture the isobutanal and the acetone in the stream to be treated and to obtain an outlet stream having isobutanal and acetone contents that are reduced compared to the contents of the initial stream, or even to completely eliminate the isobutanal and acetone. In particular, the contents by weight or molar contents of isobutanal and acetone in the effluent after treatment according to the invention can be reduced by at least 90%, preferably at least 95%, and more preferably at least 99% relative to the corresponding contents in the olefinic feedstock before treatment.

The use of such a process but under conditions other than those defined, in particular at higher temperatures, in particular above 200° C., could lead to lower adsorption capacities.

According to a preferred embodiment of the present invention, the purification of the olefinic feedstock, in particular the simultaneous elimination of isobutanal and acetone, is carried out in a reactor comprising several fixed beds which are placed in parallel and which are interchangeable. Thus, it is possible to take away one of the guard beds for the purpose of regeneration when the adsorbent(s) constituting it are saturated with impurities, this being without stopping the flow rate of the feedstock and therefore without stopping production.

Several options can be envisioned for the phase for regeneration of the fixed bed or saturated guard bed.

According to a first embodiment, the saturated guard bed can be extracted from the reactor. In this case, it is advantageously possible to eliminate the liquid, for example by stripping, then the solid and to clean this part of the reactor. Reloading can advantageously be done with a new adsorbent feedstock, or with the old adsorbent feedstock, regenerated with solvent, for example by passing a solvent between 30 and 200° C., or by burning, before putting this part back in the reactor.

According to a second embodiment, the regeneration of the saturated adsorbent bed can advantageously be carried out by online cocurrent or countercurrent rinsing with a solvent in order to desorb the impurities adsorbed in the adsorption step. The solvent is advantageously a light hydrocarbon chosen from pentane, heptane or hexane. According to one embodiment of the invention, the solvent can be heated to a temperature of between 30 and 350° C. The pressure is between 0.1 and 10 MPa, preferably between 0.3 and 5 MPa. After separation at the reactor outlet of the impurities adsorbed during the adsorption phase and extracted during this regeneration of the adsorbent, and of the regeneration solvent, the solvent is advantageously recycled to the reactor to continue the regeneration.

According to a third embodiment, the phase for regeneration of the guard bed saturated with impurities is advantageously carried out by passing a gas between 180 and 500° C. The gas used can be a combustion gas, air or nitrogen. Preferably the regeneration gas is nitrogen. According to a variant of the invention, the regeneration gas can contain water, between a few ppm by volume and 40% by volume of water, preferably between 0.1 and 20% by volume and even more preferably between 0.1 and 10% by volume.

Preferably, the regeneration of the adsorbent is carried out in situ. Even more preferably, the regeneration of the adsorption takes place in situ with a hot gas.

In the case where the purification according to the invention is carried out in an interchangeable fixed bed of at least one adsorbent comprising at least one material with a zeolite framework, the interchanging is advantageously carried out when the content of oxygen-containing hydrocarbon-based impurities, in the mixture of butenes after passing over the adsorbent comprising at least one material with a zeolite framework, is greater than 10 ppm by mass, preferably greater than 5 ppm by mass and even more preferably greater than 1 ppm by mass.

Preferably, said process for purifying olefins according to the invention is used upstream of any olefin conversion process or step. In a preferred embodiment, said purification process can be placed upstream of a process for metathesis of said olefins. In the case where said purification process is placed upstream of a metathesis process, the purified olefin mixture constitutes the feedstock of the metathesis process.

The examples which follow are presented by way of illustration and without limitation.

BRIEF DESCRIPTION OF THE DRAWINGS

FIG. 1 shows the acetone and isobutanal breakthrough curves obtained during the test for co-adsorption on the NaY zeolite formed with clay according to example A and under conditions of test 3 of table 1.

EXAMPLES

In examples A, B, C and E below, the ethanol and water in the olefinic feedstock were removed beforehand. The olefinic feedstock was in fact washed with water and then dried on a 3A sieve. At the end of this pre-treatment, the water and ethanol contents of the feedstock are verified respectively by the Karl Fischer method and by gas phase chromatography according to the UOP 960 method. The olefinic feedstock which is tested in examples A, B, C and E no longer contains either water or ethanol.

In example D below, the olefinic feedstock was passed over a 3A sieve beforehand. Analysis by the Karl Fischer method shows that, at the end of this pre-treatment, the olefinic feedstock tested in example D no longer contains water.

Example A. Co-Adsorption of Isobutanal and Acetone and Production of Purified Butenes An NaY zeolite from Zeolyst, formed with clay, the clay representing 15% by weight of the total weight of the adsorbent formed, is tested in a reactor, on a fixed bed at 30° C. at 0.8 MPa. The formed zeolite is white in color. The feedstock consists of 80% n-butene and 20% isobutene and comprises isobutanal and acetone in variable concentrations (cf. table 1, tests 1 to 3).

The column of adsorbent is pre-activated at 350° C. under $N_2$ for 12 h and is then filled with butane at 30° C. at 0.8 MPa. A switch is then made to the feedstock which is injected at a flow rate of 0.5 ml/min continuously, i.e. an HSV of 0.5 $h^{-1}$.

The concentration of the various constituents at the outlet of the reactor is monitored by means of a gas phase chromatography analysis on a microGC 4900 from Varian. The test is considered to be complete when the concentration of the outlet effluent is the same as that of the inlet feedstock, that is to say at saturation of the adsorbent.

At the end of each test, the NaY zeolite is discharged. It is systematically white in color.

The isobutanal and acetone capture capacities of the adsorbent at saturation are calculated by material balance between what enters and what leaves the column. These capture capacities, expressed in g per 100 g of adsorbent, are reported in table 1 along with the isobutanal and acetone concentrations of the olefinic feedstock, expressed in ppm by mass, and their molar ratio.

TABLE 1

Amounts of isobutanal and acetone adsorbed by NaY from feedstocks containing variable ratios of isobutanal and acetone

| Test | [Isobutanal] (ppm by mass) | [Acetone] (ppm by mass) | Isobutanal/ acetone molar ratio | $q_{ads\_isobutanal}$ (g/100 g) | $q_{ads\_acetone}$ (g/100 g) |
|---|---|---|---|---|---|
| 1 | 1922 | 1552 | 1 | 8.2 | 10.4 |
| 2 | 645 | 435 | 1.2 | 9.1 | 9.8 |
| 3 | 638 | 105 | 5 | 8.1 | 3.3 |

The values of capture capacities obtained ($q_{ads\_isobutanal}$, $q_{ads\_acetone}$) show that the NaY zeolite makes it possible to significantly capture the isobutanal and acetone present in the starting olefinic feedstock, whatever the isobutanal and acetone concentrations and concentration ratio.

The isobutanal and acetone breakthrough curves obtained during the test for co-adsorption of isobutanal and acetone present in the feedstock at respective concentrations of 638 and 105 ppm by mass, on the NaY zeolite formed with clay (test 3 according to the invention in table 1), are shown in FIG. 1.

According to FIG. 1, it appears that the process according to the invention, carried out on a bed of FAU type zeolite (NaY zeolite) at 30° C., makes it possible to obtain isobutanal and acetone contents in the effluent at the column outlet of less than 1 ppm by mass. Indeed, the concentrations of isobutanal and acetone in the reactor outlet effluent are both lower than the limit of detection of 1 ppm by mass, for 155 and 230 minutes respectively for isobutanal and acetone.

Example B. Co-Adsorption of Isobutanal and Acetone on a 5A Zeolite of LTA Type (Comparative Example A test similar to that of example A is carried out on a 5A zeolite of LTA structural type (formed with 15% by weight of clay) of which the cages have, as maximum opening, a ring consisting of 8 oxygen atoms, with a feedstock consisting of 80% n-butene, 20% isobutene, 647 ppm by mass of isobutanal and 103 ppm by mass of acetone.

The capture capacities expressed in g per 100 g of adsorbent are reported in table 2 along with the isobutanal and acetone concentrations of the olefinic feedstock, expressed in ppm by mass, and their molar ratio, and compared to those obtained in test 3 of the table 1 of example A carried out with the same feedstock.

TABLE 2

Amounts of isobutanal and acetone adsorbed by the NaY and by the 5A zeolite

| Zeolite | [Isobutanal] (ppm by mass) | [Acetone] (ppm by mass) | Isobutanal/ acetone molar ratio | $q_{ads\_isobutanal}$ (g/100 g) | $q_{ads\_acetone}$ (g/100 g) |
|---|---|---|---|---|---|
| NaY | 638 | 105 | 5 | 8.1 | 3.3 |
| 5A | 647 | 103 | 5 | 0.6 | 2.1 |

These results show that the 5A zeolite of LTA structural type of which the cages have, as maximum opening, a ring consisting of 8 oxygen atoms adsorbs almost no isobutanal. This LTA-type zeolite has cages with an opening that is too small to allow the isobutanal to enter. It is therefore necessary to use zeolites of which at least one opening consists of a ring of at least 10 oxygen atoms.

Example C. Co-Adsorption of Isobutanal and Acetone on an Alumina Adsorbent (Comparative Example A test similar to that of example A is carried out on an alumina with a feedstock consisting of 80% n-butene, 20% isobutene, 644 ppm by mass of isobutanal and 107 ppm by mass of acetone. The alumina adsorbent is initially white in color.

After the test, the discharged alumina is orange. This is due to a breakdown of the isobutanal and acetone which have reacted together. This adsorbent is therefore not suitable for purifying feedstocks containing these two compounds since the product resulting from the reaction between the isobutanal and the acetone is less well retained by the adsorbent and therefore results in a loss of capture capacity of the adsorbent.

Example D. Co-Adsorption of Isobutanal and Acetone of a Feedstock Also Containing Ethanol and Production of Purified Butenes (Comparative Example)

A test similar to that of example A is carried out with a feedstock composed of 80% n-butene and 20% isobutene and comprising an almost equimolar mixture of isobutanal (499 molar ppm, i.e. 642 ppm by mass), acetone (503 molar ppm, i.e. 521 ppm by mass) and ethanol (501 molar ppm, i.e. 412 ppm by mass).

The saturation adsorption capacity of the NaY zeolite (formed with 15% by weight of clay), expressed in g/100 g of the NaY zeolite, for isobutanal, acetone and ethanol is respectively 0.9 g/100 g, 1.2 g/100 g and 17.6 g/100 g. The presence of ethanol in an almost equimolar amount relative to isobutanal and acetone leads to a reduction in the isobutanal and acetone adsorption capacities of NaY by a factor close to 10. These results show that the presence of ethanol is very strongly unfavorable to the capture of isobutanal and acetone by NaY.

Example E. Regenerability of the Adsorbent and Cycling

An NaY zeolite from Zeolyst formed with 15% clay is tested on a fixed bed at 30° C. at 0.8 MPa, at a flow rate of the olefinic feedstock of 0.5 ml/min, i.e., an HSV of 0.5 $h^{-1}$. The feedstock is composed of 80% n-butene and 20% isobutene and comprises 638 ppm by mass of isobutanal and 105 ppm by mass of acetone.

The concentrations of isobutanal and acetone in the outlet effluent are monitored by gas phase chromatography analysis on a microGC 4900 from Varian.

When the composition at the outlet becomes identical to that at the inlet, the adsorbent is considered to be saturated. The flow rate of the feedstock is stopped and the adsorbent is regenerated under a nitrogen stream at atmospheric pressure at 290° C., at 20 NL/h. Regeneration is considered to be complete when the concentrations of isobutanal and acetone in the outlet stream become zero. The nitrogen stream is then replaced by an olefinic feedstock stream, having the same flow rate and same composition as the feedstock of the $1^{st}$ cycle so as to carry out a second isobutanal and acetone adsorption cycle. The outlet concentrations are monitored as previously by gas phase chromatography analysis on a microGC 4900. When the composition at the outlet becomes identical to that at the inlet, the column is again subjected to a nitrogen stream at atmospheric pressure at 290° C.

5 adsorption/regeneration cycles (the last regeneration not being carried out) are carried out one after the other. The isobutanal and acetone capture capacities, calculated in the same way as in example A, are shown in table 3.

TABLE 3

Amounts of isobutanal and acetone adsorbed by the NaY zeolite after each of the 5 adsorption/desorption cycles

| Cycle | $q_{ads\_isobutanal}$ (g/100 g) | $q_{ads\_acetone}$ (g/100 g) |
|---|---|---|
| 1 | 8.1 | 3.3 |
| 2 | 6.0 | 2.8 |
| 3 | 5.1 | 2.7 |
| 4 | 5.4 | 2.7 |
| 5 | 5.2 | 2.7 |

After five adsorption cycles and four regenerations, the isobutanal and acetone adsorption capacities of the NaY zeolite tested are still satisfactory. The NaY adsorbent is still able to jointly eliminate isobutanal and acetone.

The invention claimed is:

1. A process for purifying an olefinic feedstock comprising olefins with 4 carbon atoms and impurities including isobutanal, ethanol and acetone, said process comprising:
   a) a pre-treatment step comprising at least a step of eliminating the ethanol and water;
   b) a step of simultaneously eliminating the isobutanal and the acetone, by passing the pretreated feedstock from step a) over at least one fixed bed of at least one adsorbent comprising at least one material with a zeolite framework,
   said material with a zeolite framework being chosen from the group consisting of: zeolites, AlPOs, SAPOs and mixtures thereof;
   said material with a zeolite framework having at least cages or channels of which at least one opening is defined by a ring comprising at least 10 oxygen atoms (10MR);
   said step b) being carried out at a temperature of between 0 and 200° C., at a pressure of 0.1 to 10 MPa and with an hourly space velocity (HSV) of the pretreated feedstock from step a) over the fixed bed of between 0.1 and 10 $h^{-1}$.

2. The process as claimed in claim 1, wherein said olefinic feedstock results from the dehydration of isobutanol or of a mixture of butanol isomers comprising isobutanol.

3. The process as claimed in claim 1, wherein the ethanol is eliminated by washing the olefinic feedstock with water followed by drying.

4. The process as claimed in claim 1, wherein the zeolite is chosen from the types FAU, BEA, MOR, MFI, FER, EMT, TON, SZR, LTL.

5. The process as claimed in claim 1, wherein the material with a zeolite framework has an FAU structural type.

6. The process as claimed in claim 1, wherein the material with a zeolite framework has one or more types of charge-compensating cations.

7. The process as claimed in claim 6, wherein the charge-compensating cation(s) are alkali metals.

8. The process as claimed in claim 1, wherein the material with a zeolite framework is formed with a binder chosen from simple or mixed refractory oxides or hydroxides, clays, active carbons, and crosslinked vinyl resins, and such that the binder content is between 5 and 30% by weight of the adsorbent.

9. The process as claimed in claim 1, wherein step b) is carried out at a temperature of between 20 and 60° C.

10. The process as claimed in claim 1, wherein step b) is carried out at a pressure of between 0.3 and 5 MPa.

11. The process as claimed in claim 1, wherein step b) is carried out such that the hourly space velocity (HSV) of said feedstock on said fixed bed is between 0.2 and 5 $h^{-1}$.

12. The process as claimed in claim 1, wherein step b) is carried out in a reactor comprising several fixed beds which are placed in parallel and which are interchangeable.

13. A process for converting olefins, comprising a step corresponding to the process for purifying the olefinic feedstock as claimed in claim 1, upstream of the metathesis process.

* * * * *